United States Patent
Sato (10) Patent No.: US 10,143,688 B2
(45) Date of Patent: Dec. 4, 2018

(54) MESYLIC ACID SALT OF ACYLTHIOUREA COMPOUND, CRYSTAL OF THE SAME, AND PROCESS FOR PRODUCING THESE

(71) Applicant: TAIHO PHARMACEUTICAL CO., LTD., Chiyoda-ku (JP)

(72) Inventor: Ayako Sato, Ibaraki (JP)

(73) Assignee: TAIHO PHARMACEUTICAL CO., LTD., Chiyoda-ku (JP)

( * ) Notice: Subject to any disclaimer, the term of this patent is extended or adjusted under 35 U.S.C. 154(b) by 0 days.

(21) Appl. No.: 15/570,021

(22) PCT Filed: Apr. 28, 2016

(86) PCT No.: PCT/JP2016/063413
§ 371 (c)(1),
(2) Date: Oct. 27, 2017

(87) PCT Pub. No.: WO2016/175305
PCT Pub. Date: Nov. 3, 2016

(65) Prior Publication Data
US 2018/0161317 A1 Jun. 14, 2018

(30) Foreign Application Priority Data
Apr. 30, 2015 (JP) ................. 2015-092815

(51) Int. Cl.
*C07D 215/48* (2006.01)
*A61K 31/47* (2006.01)
*A61P 35/00* (2006.01)
*A61K 9/00* (2006.01)
*A61K 31/17* (2006.01)

(52) U.S. Cl.
CPC ............ *A61K 31/47* (2013.01); *A61K 9/0053* (2013.01); *A61K 31/17* (2013.01); *A61P 35/00* (2018.01); *C07D 215/48* (2013.01)

(58) Field of Classification Search
CPC .................................................. C07D 215/48
See application file for complete search history.

(56) References Cited

U.S. PATENT DOCUMENTS
9,149,471 B2  10/2015 Miyaura et al.
2011/0034439 A1  2/2011 Suda et al.

FOREIGN PATENT DOCUMENTS
WO  2009/125597 A1  10/2009
WO  2015/046484 A1  4/2015

OTHER PUBLICATIONS

International Search Report dated Jun. 28, 2016, in PCT/JP2016/063413, filed Apr. 28, 2016.
Ashizawa K., "Polymorphic Phenomena of Drug and Science of Crystallization Development and Production and Trend of Regulation", Iyakuhin no Takei Gensho to Shoseki no Kagaku, 2002, 77 pages. (with English translation).
Caira M., "Crystalline Polymorphism of Organic Compounds", Topics in Current Chemistry, vol. 198, 1998, pp. 163-208.
Anderson B. et al., (Edited by Wermuth, C.G), "Preparation of Water-Soluble Organic Compounds Through Salt Formation", Saishin Soyaku Kagaku last volume, 1999, 65 pages. (with English translation).
Berge S. et al., "Pharmaceutical Salts", Journal of Pharmaceutical Sciences, vol. 66, No. 1, Jan. 1977, pp. 1-19.

*Primary Examiner* — Bruck Kifle
(74) *Attorney, Agent, or Firm* — Oblon, McClelland, Maier & Neustadt, L.L.P.

(57) ABSTRACT

An object of the present invention is to provide a salt compound of 4-(2-fluoro-4-(3-(2-phenylacetyl)thioureido)phenoxy)-7-methoxy-N-methylquinoline-6-carboxamide, which is useful as an antitumor agent, and crystal of the salt. The salt and the crystal are excellent in terms of solubility, stability, and peroral absorbability and can be mass-produced. The present invention relates to: a mesylic acid salt of 4-(2-fluoro-4-(3-(2-phenylacetyl)thioureido)phenoxy)-7-methoxy-N-methylquinoline-6-carboxamide; and the mesylic acid salt including a crystal which gives an X-ray powder diffraction spectrum having characteristic peaks at specific diffraction angles.

20 Claims, 8 Drawing Sheets

MESYLIC ACID SALT OF ACYLTHIOUREA COMPOUND, CRYSTAL OF THE SAME, AND PROCESS FOR PRODUCING THESE

TECHNICAL FIELD

The present invention relates to a mesylic acid salt of an acylthiourea compound, in particular, the mesylic acid salt in the form of crystals, the salt being excellent in terms of solubility and peroral absorbability and useful as an antitumor agent. The invention further relates to a medicinal composition containing the mesylic acid salt of an acylthiourea compound, in particular, a medicinal composition for oral administration. The invention furthermore relates to a process for producing the mesylic acid salt of an acylthiourea compound or for producing a crystal of the salt.

BACKGROUND ART

In general, the active ingredients of medicinal compositions for oral administration are required, for example, to be excellent in terms of solubility, stability, and peroral absorbability and be produced by a method capable of mass production. In the case of an active ingredient which is an organic compound, salts of the active ingredient are investigated in order to improve the solubility, etc., but it is difficult to predict an optimal salt.

In the case of a compound which exhibits crystal polymorphism, the crystal polymorphs are crystal forms which differ in the arrangement of atoms or molecules in the crystal although having the same molecule. The crystal polymorphs differ in the peaks obtained by X-ray powder diffractometry (XRD). It is also known that the crystal polymorphs differ in solubility, stability, peroral absorbability, etc., and it is required for developing medicines to find out a crystal form which is optimal from various standpoints.

At present, a plurality of inhibitors each combine c-Met inhibitory activity and VEGFR2 inhibitory activity have been reported as antitumor agents. As a compound having excellent c-Met/VEGFR2 inhibitory activity and showing antitumor activity, 4-(2-fluoro-4-(3-(2-phenylacetyl)thioureido)phenoxy)-7-methoxy-N-methylquinoline-6-carboxamide (hereinafter referred to also as "compound 1") has been reported (Patent Documents 1 and 2 and Non-Patent Documents 1 and 2). It has also been reported that compound 1 is useful as a therapeutic agent for osteoporosis (Patent Document 3).

PRIOR ART DOCUMENTS

Patent Documents

Patent Document 1: International Publication WO 2009/125597
Patent Document 2: International Publication WO 2013/100014
Patent Document 3: International Publication WO 2015/046484

Non-Patent Documents

Non-Patent Document 1: *Molecular Cancer Therapeutics;* 12(12); pp. 2685-96, 2013
Non-Patent Document 2: *European Journal of Cancer;* 48(6); p. 94; 2012

SUMMARY OF THE INVENTION

Problems that the Invention is to Solve

However, these reports contain no mention of the solubility, stability, or peroral absorbability of any salt of 4-(2-fluoro-4-(3-(2-phenylacetyl)thioureido)phenoxy)-7-methoxy-N-methylquinoline-6-carboxamide (compound 1) or of crystals of the salt, and any process for producing these is not described or suggested therein at all.

Meanwhile, compound 1 in the free form, i.e., not in a salt form, was found to be low in solubility and peroral absorbability.

Accordingly, an object of the invention is to provide a salt of compound 1 and crystals of the salt, the salt and the crystals being useful as an antitumor agent and a therapeutic agent for osteoporosis, excellent in terms of solubility, stability, and peroral absorbability, and capable of being pass-produced.

Means for Solving the Problems

The present inventor diligently made investigations and, as a result, have discovered that a mesylic acid salt of 4-(2-fluoro-4-(3-(2-phenylacetyl)thioureido)phenoxy)-7-methoxy-N-methylquinoline-6-carboxamide is excellent in terms of solubility and peroral absorbability and that crystals of the mesylic acid salt are excellent in terms of solubility, stability, and peroral absorbability and can be mass-produced. The present invention has been thus completed.

The present invention relates to the following [1] to [23].
[1] A mesylic acid salt of 4-(2-fluoro-4-(3-(2-phenylacetyl)thioureido)phenoxy)-7-methoxy-N-methylquinoline-6-carboxamide.
[2] The salt according to [1],
which comprises a crystal that gives an X-ray powder diffraction spectrum having characteristic peaks at at least three diffraction angles (2θ±0.2°) selected from among 6.7°, 7.9°, 9.6°, 12.5°, 13.8°, 19.8°, 21.2°, and 26.1°.
[3] The salt according to [1],
which comprises a crystal that gives an X-ray powder diffraction spectrum having characteristic peaks at at least five diffraction angles (2θ±0.2°) selected from among 6.7°, 7.9°, 9.6°, 12.5°, 13.8°, 19.8°, 21.2°, and 26.1°.
[4] The salt according to [1],
which comprises a crystal that gives an X-ray powder diffraction spectrum having characteristic peaks at diffraction angles (2θ±0.2°) of 6.7°, 7.9°, 9.6°, 12.5°, 13.8°, 19.8°, 21.2°, and 26.1°.
[5] The salt according to any one of [1] to [4],
which shows an endothermic peak at 217±5° C. in differential thermal analysis.
[6] A medicinal composition
which contains the salt according to any one of [1] to [5].
[7] A medicinal composition for oral administration
which contains the salt according to any one of [1] to [5].
[8] A process for producing a mesylic acid salt of 4-(2-fluoro-4-(3-(2-phenylacetyl)thioureido)phenoxy)-7-methoxy-N-methylquinoline-6-carboxamide or for producing a crystal of the salt, the process comprising:
step (1), which is a step in which 4-(2-fluoro-4-(3-(2-phenylacetyl)thioureido)phenoxy)-7-methoxy-N-methylquinoline-6-carboxamide and mesylic acid are added to a solvent; and
step (2), which is a step in which the solvent obtained in step (1) above is stirred to precipitate a mesylic acid salt of 4-(2-fluoro-4-(3-(2-phenylacetyl)thioureido)phenoxy)-7-methoxy-N-methylquinoline-6-carboxamide.

[9] The process for production according to [8],
wherein the mesylic acid salt of 4-(2-fluoro-4-(3-(2-phenylacetyl)thioureido)phenoxy)-7-methoxy-N-methylquinoline-6-carboxamide or the crystal of the salt gives an X-ray powder diffraction spectrum having characteristic peaks at at least three diffraction angles (2θ±0.2°) selected from among 6.7°, 7.9°, 9.6°, 12.5°, 13.8°, 19.8°, 21.2°, and 26.1°.

[10] The process for production according to [8],
wherein the mesylic acid salt of 4-(2-fluoro-4-(3-(2-phenylacetyl)thioureido)phenoxy)-7-methoxy-N-methylquinoline-6-carboxamide or the crystal of the salt gives an X-ray powder diffraction spectrum having characteristic peaks at at least five diffraction angles (2θ±0.2°) selected from among 6.7°, 7.9°, 9.6°, 12.5°, 13.8°, 19.8°, 21.2°, and 26.1°.

[11] The process for production according to [8],
wherein the mesylic acid salt of 4-(2-fluoro-4-(3-(2-phenylacetyl)thioureido)phenoxy)-7-methoxy-N-methylquinoline-6-carboxamide or the crystal of the salt gives an X-ray powder diffraction spectrum having characteristic peaks at diffraction angles (2θ±0.2°) of 6.7°, 7.9°, 9.6°, 12.5°, 13.8°, 19.8°, 21.2°, and 26.1°.

[12] The process for production according to any one of [8] to [11],
wherein the mesylic acid salt of 4-(2-fluoro-4-(3-(2-phenylacetyl)thioureido)phenoxy)-7-methoxy-N-methylquinoline-6-carboxamide or the crystal of the salt shows an endothermic peak at 217±5° C. in differential thermal analysis.

[13] The process for production according to any one of [8] to [12],
wherein the solvent in step (1) is water, an alcohol, an aliphatic carboxylic acid ester, a ketone, an ether, a hydrocarbon, an aprotic polar solvent, or a mixed solvent composed of two or more of these.

[14] The process for production according to any one of [8] to [13],
wherein the solvent in step (1) is water, an alcohol, an aliphatic carboxylic acid ester, a ketone, or a mixed solvent composed of two or more of these.

[15] The process for production according to any one of [8] to [14],
wherein the solvent in step (1) is ethanol, isopropanol, ethyl acetate, acetone, methyl ethyl ketone, methyl isobutyl ketone, or an acetone/water mixed solvent.

[16] A mesylic acid salt of 4-(2-fluoro-4-(3-(2-phenylacetyl)thioureido)phenoxy)-7-methoxy-N-methylquinoline-6-carboxamide, the salt having been produced by a process for production comprising:
step (1), which is a step in which 4-(2-fluoro-4-(3-(2-phenylacetyl)thioureido)phenoxy)-7-methoxy-N-methylquinoline-6-carboxamide and mesylic acid are added to a solvent; and
step (2), which is a step in which the solvent obtained in step (1) above is stirred to precipitate a mesylic acid salt of 4-(2-fluoro-4-(3-(2-phenylacetyl)thioureido)phenoxy)-7-methoxy-N-methylquinoline-6-carboxamide.

[17] The salt according to [16],
which comprises a crystal that gives an X-ray powder diffraction spectrum having characteristic peaks at at least three diffraction angles (2θ±0.2°) selected from among 6.7°, 7.9°, 9.6°, 12.5°, 13.8°, 19.8°, 21.2°, and 26.1°.

[18] The salt according to [16],
which comprises a crystal that gives an X-ray powder diffraction spectrum having characteristic peaks at at least five diffraction angles (2θ±0.2°) selected from among 6.7°, 7.9°, 9.6°, 12.5°, 13.8°, 19.8°, 21.2°, and 26.1°.

[19] The salt according to [16],
which comprises a crystal that gives an X-ray powder diffraction spectrum having characteristic peaks at diffraction angles (2θ±0.2°) of 6.7°, 7.9°, 9.6°, 12.5°, 13.8°, 19.8°, 21.2°, and 26.1°.

[20] The salt according to any one of [16] to [19],
which shows an endothermic peak at 217±5° C. in differential thermal analysis.

[21] The salt according to any one of [16] to [20],
wherein the solvent in step (1) is water, an alcohol, an aliphatic carboxylic acid ester, a ketone, an ether, a hydrocarbon, an aprotic polar solvent, or a mixed solvent composed of two or more of these.

[22] The salt according to any one of [16] to [21],
wherein the solvent in step (1) is water, an alcohol, an aliphatic carboxylic acid ester, a ketone, or a mixed solvent composed of two or more of these.

[23] The salt according to any one of [16] to [22],
wherein the solvent in step (1) is ethanol, isopropanol, ethyl acetate, acetone, methyl ethyl ketone, methyl isobutyl ketone, or an acetone/water mixed solvent.

Effects of the Invention

According to the present invention, the mesylic acid salt of compound 1 is excellent in terms of solubility and peroral absorbability. The crystal of the mesylic acid salt of compound 1 according to the invention is excellent in terms of solubility, stability, and peroral absorbability and can be mass-produced. The salt and the crystal can hence be expected to be utilized as medicines, in particular, medicines for oral administration.

MODES FOR CARRYING OUT THE INVENTION

The compound, a mesylic acid salt of which is formed in the present invention, is 4-(2-fluoro-4-(3-(2-phenylacetyl)thioureido)phenoxy)-7-methoxy-N-methylquinoline-6-carboxamide (compound 1). The structure thereof is shown below.

Compound 1 is one of the acylthiourea compounds which are known to have c-Met/VEGFR inhibitory activity and exhibit excellent antitumor activity.

[Chem. 1]

(Compound 1)

It is generally known that salts of organic compounds have better solubility in water than the organic compounds themselves. In the case of organic compounds which themselves are basic, these organic compounds are capable of forming salts with various acids. In the case of organic compounds which are acidic, these organic compounds not only are likewise capable of forming salts with various bases but also are capable of forming salts when hydrogen atoms which can be liberated are replaced with alkali metal ions, alkaline earth metal ions, transition metal ions, etc. The thus-formed salts of organic compounds can be obtained usually as liquids or solids. In the case where an organic compound itself has a problem when developing a medicine, it is required to find out an optimal salt to overcome the problem.

The term crystal means a solid in which the atoms or molecules have been arranged so as to form a regular repeating structure, and the crystal differs from amorphous solids, which have no repeating structure. Crystalline or amorphous solids can be examined by X-ray powder diffractometry (XRD), differential scanning calorimetry (DSC), simultaneous thermogravimetry/differential thermal analysis (TG-DTA), infrared spectroscopy (IR), or the like.

The term "crystal polymorphs" means crystal forms which differ in the arrangement of atoms or molecules in the crystal although having the same molecule, and it is known that the crystal polymorphs differ in the peaks obtained by XRD. It is also known that the crystal polymorphs differ in solubility, peroral absorbability, stability, etc., and it is required to find out a crystal which is optimal for developing medicines, from various standpoints.

The present inventor diligently made investigations and, as a result, have discovered that compound 1 forms a satisfactory salt with mesylic acid and that this mesylic acid salt of compound 1 is highly excellent in terms of solubility and peroral absorbability. Furthermore, the inventor have discovered that crystals of the mesylic acid salt of compound 1 are highly excellent in terms of solubility, stability, and peroral absorbability and of production process capable of mass production.

The present invention is explained below in detail.

As stated above, compound 1 in this description is 4-(2-fluoro-4-(3-(2-phenylacetyl)thioureido)phenoxy)-7-methoxy-N-methylquinoline-6-carboxamide. The term "compound 1" means the compound in the free form, i.e., not in a salt form.

Compound 1 can be synthesized on the basis of the production process described in Patent Document 1.

There are two crystal polymorphs (crystal I and crystal II) of compound 1.

Crystal I of compound 1 is obtained by adding an N,N-diethylacetamide/isopropanol mixed solvent to compound 1, as shown in Reference Example 1, which will be given later.

Meanwhile, crystal II of compound 1 is obtained by adding ethanol to compound 1, as shown in Comparative Example 3, which will be given later. However, crystal I and crystal II of compound 1 have been unsatisfactory with respect to solubility and peroral absorbability required of medicines.

Compound 1 is basic and hence forms salts with acids. Examples of acid salts which are generally pharmaceutically acceptable include a large number of salts with: inorganic acids such as hydrochloric acid, hydrobromic acid, hydriodic acid, sulfuric acid, nitric acid, and phosphoric acid; and organic acids such as formic acid, acetic acid, propionic acid, oxalic acid, malonic acid, succinic acid, ascorbic acid, isoascorbic acid, mandelic acid, fumaric acid, aspartic acid, maleic acid, lactic acid, malic acid, hippuric acid, glutaric acid, adipic acid, citric acid, tartaric acid, carbonic acid, picric acid, methanesulfonic acid (mesylic acid), p-toluenesulfonic acid (p-tosic acid), and glutamic acid.

Test Example 1, which will be given later, suggested that the oxalic acid salt, malonic acid salt, tartaric acid salt, citric acid salt, mandelic acid salt, fumaric acid salt, aspartic acid salt, sulfuric acid salt, malic acid salt, hippuric acid salt, glutaric acid salt, adipic acid salt, succinic acid salt, ascorbic acid salt, maleic acid salt, and isoascorbic acid salt, among the salts with the acids shown above, have far lower solubility in water than the mesylic acid salt, p-toric acid salt, and hydrochloric acid salt.

Furthermore, although the salts with p-tosic acid salt and hydrochloric acid salt, among those acids, are frequently used in medicines, these salts are inferior in solubility to the mesylic acid salt of compound 1, as will be shown in Test Example 2, which will be given later. It is highly probable that these salts show reduced peroral absorbability when developing medicines.

In contrast, the mesylic acid salt of compound 1 according to the invention (hereinafter often referred to simply as "mesylic acid salt of the invention") is excellent in terms of solubility and peroral absorbability. Crystal of the mesylic acid salt are excellent in terms of solubility, stability, and peroral absorbability, can be mass-produced, and are hence suitable for use as a salt for developing medicines.

The mesylic acid salt of the invention is a salt configured of mesylic acid and compound 1 in a molar ratio of 1:1, and the molar ratio can be determined by an analysis, e.g., $^1$H-NMR spectroscopy. Usually, in a salt of an organic compound with mesylic acid, the molar ratio between the mesylic acid and the organic compound can be determined by comparing the integral of the protons of the methyl of mesylic acid with the integral of at least one proton of the organic compound. It is known that the integrals of the protons include errors due to corrections regarding the base line of the $^1$H-NMR chart, etc. Because of this, in cases when the molar ratio between mesylic acid and the organic compound is in the range of 0.8:1 to 1.2:1, the molar ratio can be regarded as 1:1.

The mesylic acid salt of the invention may be any of: a single crystal form; a mixture of two or more polymorphs; the amorphous salt; and a mixture of two or more thereof. However, the mesylic acid salt is desirably one including crystal, preferably one including crystal in an amount of 50% or larger in terms of weight ratio, more preferably one including crystal in an amount of 90% or more in terms of weight ratio. It is even more preferable that the crystal contained in the mesylic acid salt of the invention should give an X-ray powder diffraction spectrum which has the characteristic peaks that will be described later.

The crystals of the mesylic acid salt of the invention include crystals having a crystal habit, which differ in outer shape due to a difference in the growth of the crystal planes. Because of this, the crystal, upon an examination by XRD, give patterns which are equal in diffraction angle 2θ peaks but differ in the relative intensity of a peak. The term "relative intensity" herein means the relative value of the area of each diffraction angle 2θ peak in the X-ray powder diffraction spectrum, with the intensity of the peak which is largest in area being taken as 100.

In addition, the error range of each diffraction angle 2θ in the X-ray powder diffraction spectrum in the present invention is about ±0.2°. This is a range of errors due to the apparatus used for the measurement, methods used for sample preparation and for data analysis, etc. Hence, in cases when crystal in the invention is examined by XRD, the obtained diffraction angle 2θ errors of ±0.2° are taken into account.

It is preferable that a crystal of the mesylic acid salt of the invention should give an X-ray powder diffraction spectrum having characteristic peaks at at least three diffraction angles (2θ±0.2°) selected from among 6.7°, 7.9°, 9.6°, 12.5°, 13.8°, 19.8°, 21.2°, and 26.1°. In a more preferred embodiment, a crystal of the mesylic acid salt of the invention gives an X-ray powder diffraction spectrum having characteristic peaks at at least five diffraction angles (2θ±0.2°) selected from among 6.7°, 7.9°, 9.6°, 12.5°, 13.8°, 19.8°, 21.2°, and 26.1°. In an even more preferred embodiment, a crystal of the mesylic acid salt of the invention gives an X-ray powder diffraction spectrum having characteristic peaks at diffraction angles (2θ±0.2°) of 6.7°, 7.9°, 9.6°, 12.5°, 13.8°, 19.8°, 21.2°, and 26.1°. In an especially preferred embodiment, a crystal of the mesylic acid salt of the invention shows peaks at diffraction angles (2θ) of 6.7°, 7.9°, 9.6°, 11.6°, 12.5°, 13.2°, 13.8°, 14.8°, 15.7°, 19.8°, 21.2°, 23.0°, 24.5°, and 26.1°.

The temperatures at which endothermic peaks appear in a DTA curve obtained by DTA can include errors depending on heating rate, sample purity, etc. Hence, when the crystals of the invention are examined by DTA, an error range of ±5.0° C. is taken into account for each endothermic peak (peak top value). The word "around" used for taking account of such an error means ±5.0° C. The DTA may be either DTA alone or TG-DTA, which is simultaneous thermogravimetry/differential thermal analysis. However, the value for each endothermic peak obtained by differential thermal analysis in this description means [value for the peak top of each endothermic peak on a DTA curve obtained by TG-DTA]±5.0° C.

In a typical embodiment, a crystal of the mesylic acid salt of the invention gives a DTA curve which has an endothermic peak at around 217° C. (212-222° C.), as shown in the results of simultaneous thermogravimetry/differential thermal analysis shown in FIG. 6. As stated above, the term "endothermic peak" in this description means the value for the top of the peak.

It is preferable that a crystal of the mesylic acid salt of the invention should give an X-ray powder diffraction spectrum having characteristic peaks at at least three diffraction angles (2θ±0.2°) selected from among 6.7°, 7.9°, 9.6°, 12.5°, 13.8°, 19.8°, 21.2°, and 26.1°, and further give a DTA curve having an endothermic peak (peak top value) at 212-222° C. It is more preferable that a crystal of the mesylic acid salt of the invention should give an X-ray powder diffiaction spectrum having characteristic peaks at at least five diffraction angles (2θ±0.2°) selected from among 6.7°, 7.9°, 9.6°, 12.5°, 13.8°, 19.8°, 21.2°, and 26.1°, and further give a DTA curve having an endothermic peak (peak top value) at 212-222° C. It is even more preferable that a crystal of the mesylic acid salt of the invention should give an X-ray powder diffraction spectrum having characteristic peaks at diffraction angles (2θ±0.2°) of 6.7°, 7.9°, 9.6°, 12.5°, 13.8°, 19.8°, 21.2°, and 26.1°, and further give a DTA curve having an endothermic peak (peak top value) at 212-222° C. It is especially preferable that a crystal of the mesylic acid salt of the invention should show peaks at diffraction angles (2θ) of 6.7°, 7.9°, 9.6°, 11.6°, 12.5°, 13.2°, 13.8°, 14.8°, 15.7°, 19.8°, 21.2°, 23.0°, 24.5°, and 26.1°, and further give a DTA curve having an endothermic peak (peak top value) at 212-222° C.

The mesylic acid salt of the invention or crystal thereof can be obtained by adding compound 1 and mesylic acid to a specific solvent and stirring the mixture to cause precipitation. The present invention hence further provides a process for producing a mesylic acid salt of 4-(2-fluoro-4-(3-(2-phenylacetyl)thioureido)phenoxy)-7-methoxy-N-methylquinoline-6-carboxamide (compound 1) or for producing crystal of the salt, the process comprising:

(1) a step in which compound 1 and mesylic acid are added to a solvent; and (2) a step in which the solvent obtained in step (1) above is stirred to precipitate a mesylic acid salt of compound 1.

The present invention furthermore provides the mesylic acid salt of compound 1 produced by the process or the crystal thereof produced by the process.

The compound 1 to be used in the process for producing the mesylic acid salt of the invention or crystal thereof may be any of: the amorphous compound, crystal I, crystal II, another crystal form, or a mixture of two or more thereof.

The amount of the mesylic acid to be added in the process for producing the mesylic acid salt of the invention or crystal thereof is 0.1-30 times, preferably 1-10 times, more preferably 1.1-5 times, the amount of the compound 1 in terms of molar ratio.

Examples of solvents usable in the process for producing the mesylic acid salt of the invention or crystals thereof include water, alcohols, aliphatic carboxylic acid esters, ketones, ethers, hydrocarbons, and aprotic polar solvents. Also usable is a mixed solvent composed of two or more of these.

Examples of the alcohols include methanol, ethanol, n-propanol, and isopropanol. Preferred are ethanol and isopropanol.

Examples of the aliphatic carboxylic acid esters include methyl formate, ethyl formate, methyl acetate, ethyl acetate, isopropyl acetate, and butyl acetate. Preferred is ethyl acetate.

Examples of the ketones include acetone, methyl ethyl ketone, methyl isopropyl ketone, methyl isobutyl ketone, and cyclohexanone. Preferred is acetone, methyl ethyl ketone, or methyl isobutyl ketone.

Examples of the ethers include diethyl ether, t-butyl methyl ether, tetrahydrofuran, and 1,4-dioxane.

Examples of the hydrocarbons include n-hexane, n-pentane, n-heptane, cyclohexane, cyclopentane, and petroleum ether.

Examples of the aprotic polar solvents include acetonitrile, N-methyl-2-pyrrolidone, N,N-dimethylformamide, N,N-dimethylacetamide, and dimethyl sulfoxide.

Examples of solvents usable in the process for producing the mesylic acid salt of the invention or crystal thereof include the solvents shown above or mixed solvents each composed of two or more thereof. Preferred are water, alcohols, aliphatic carboxylic acid esters, ketones, or mixed solvents each composed of two or more of these. More preferred is ethanol, isopropanol, ethyl acetate, acetone, methyl ether ketone, methyl isobutyl ketone, or an acetone/water mixed solvent. Especially preferred is an acetone/water mixed solvent.

With respect to the ratio between the solvents in the acetone/water mixed solvent, the amount of the acetone per part by volume of the water is preferably 0.1-50 parts by volume, more preferably 1-20 parts by volume, even more preferably 2-10 parts by volume.

The amount of the solvent that can be used in the process for producing the mesylic acid salt of the invention or crystal thereof is 0.1-100 (volume/weight) times the amount of the compound 1. The amount thereof is preferably 1-50 (volume/weight) times, more preferably 5-30 (volume/weight) times.

The temperature in the step for precipitating the mesylic acid salt of the invention is suitably set in accordance with the solvent used, in the range of 0° C. to the boiling point of the solvent. The temperature in the step for precipitation need not be constant, and the mixture can be heated or cooled at temperatures between 0° C. and the boiling point of the solvent.

The stirring in the step for precipitating the mesylic acid salt of the invention is conducted by suitably using a stirring machine, stirring blades, magnetic stirrer, or the like in accordance with the solvent amount and the size of the reaction tank. The stirring speed is 1-600 rpm, preferably 10-300 rpm.

In general, in case where the period of stirring for precipitating salts or crystals is too short, the precipitation does not proceed sufficiently, making it impossible to obtain salts or crystals in high yield. Meanwhile, in case where the period thereof is too long, the active ingredients suffer decomposition, resulting in a decrease in yield. An appropriate period is hence set. The stirring period in the step for precipitating the mesylic acid salt of the invention is, for example, 1 minute to 120 hours, and is preferably 1-72 hours, more preferably 3-48 hours.

In the step for precipitating the mesylic acid salt of the invention, crystal of a mesylic acid salt of compound 1 may be added as seed crystal. The amount of the seed crystal to be added is 0.1-10% by weight, preferably 1-3% by weight, of a theoretical yield of the mesylic acid salt of compound 1 in the crystallization.

The mesylic acid salt of the invention which has precipitated in the solvent can be isolated and purified by known separation/purification means, such as filtration, cleaning with an organic solvent, and vacuum drying. Examples of the organic solvent for use in the cleaning include the same solvents as those usable for the production.

The atmospheric pressure in the vacuum drying is 0.1 atm or less, preferably 0.05 atm or less. The temperature in the vacuum drying is 0-200° C., preferably 25-100° C.

The present invention still further relates to a medicinal composition containing the mesylic acid salt of compound 1. In particular, since compound 1 has excellent c-Met inhibitory activity and VEGFR2 inhibitory activity, the mesylic acid salt of the invention is useful as an antitumor agent. Although cancers for which the salt of the invention is intended to be used are not particularly limited, examples thereof include head and neck cancers, digestive cancers (esophageal cancer, gastric cancer, digestive-tract interstitial tumor, duodenal cancer, hepatic cancer, biliary tract cancers (gallbladder/bile duct cancer, etc.), pancreatic cancer, small intestinal cancer, and colorectal cancers (colon/rectal cancer, colon cancer, rectal cancer, etc.)), lung cancer, mammary cancer, ovarian cancer, uterine cancers (cervical cancer, cancer of the uterine body, etc.), kidney cancer, bladder cancer, prostate cancer, urinary epithelial cancer, osteogenic/soft-part sarcoma, blood cancers (B-cell lymphoma, chronic lymphocytic leukemia, peripheral T-cell lymphoma, myelodysplastic syndrome, acute myelocytic leukemia, acute lymphocytic leukemia, etc.), multiple myeloma, skin cancer, and mesothelioma.

The medicinal composition containing the mesylic acid salt of the invention can be made to have any of various administration forms according to preventive or therapeutic purposes, by incorporating a pharmaceutical carrier according to need. Examples of the forms include a peroral preparation, injection preparation, suppository, ointment, and patch. Preferred is a peroral preparation. Namely, it is preferable that the medicinal composition according to the invention should be a medicinal composition for peroral administration. Those various forms can each be produced by a preparation method which is known to persons skilled in the art and is in common use.

As the pharmaceutical carrier, use may be made of various organic or inorganic carrier substances in common use as materials for pharmaceutical preparations. Such substances are incorporated as an excipient, binder, disintegrator, lubricant, and colorant into solid preparations or as a solvent, dissolution aid, suspending agent, isotronizing agent, buffer agent, pain-alleviating agent, etc. into liquid preparations. Furthermore, additives for pharmaceutical preparations, such as an antiseptic, antioxidant, colorant, sweetener, stabilizer, etc., can be used according to need.

In the case of producing a peroral solid preparation, an excipient is added to the mesylic acid salt of the invention, or, an excipient, binder, disintegrator, lubricant, colorant, corrective, etc. according to need is added to the mesylic acid salt of the invention, and the resultant mixture can be formed into a tablet, coated tablet, granules, powder, capsule, or the like in an ordinary manner.

In the case of producing injection preparations, ingredients such as a pH regulator, buffer agent, stabilizer, isotronizing agent, and local anesthetic are added to the mesylic acid salt of the invention, and hypodermic, intramuscular, and intravenous injection preparations can be produced therefrom in ordinary manners.

The amount of the mesylic acid salt of the invention to be incorporated into a unit package of each of the administration forms varies depending on the condition of the patient to whom the salt is to be applied or on the form itself of the preparation, etc. In general, however, it is desirable that the amount of the salt per unit package of each administration form should be 0.05-1,000 mg for the peroral preparation, 0.01-500 mg for the injection preparation, or 1-1,000 mg for the suppository.

The dose per day of the drug formulated into any of those administration forms varies depending on the condition, weight, age, and sex of the patient, etc., and cannot be unconditionally specified. However, the dose of the mesylic acid salt of the invention per day for an adult (body weight, 50 kg) may be 0.05-5,000 mg, preferably 0.1-1,000 mg, and it is preferred to perform the daily administration at a time or in multiple dosages, e.g., 2 or 3 times a day.

EXAMPLE

The present invention is explained below in more detail by reference to an Example, but the invention should not be construed as being limited by the following Example. Although the invention is sufficiently illustrated by the Example, it is to be understood that the invention can be variously changed or modified by a person skilled in the art. Consequently, any such changes or modifications are included in the present invention unless they depart from the scope of the invention.

The various reagents used in the Example were commercial products unless otherwise indicated.

<X-Ray Powder Diffractometry (XRD)>

An appropriate amount of a test specimen was lightly pulverized according to need with an agate mortar and then examined by X-ray powder diffractometry under the following test conditions.

Apparatus: Xpert PRO MPD (manufactured by Spectris Co., Ltd.)
Target: CuKα
Scanning range: 5.0-35.0°
Step size: 0.02°
Scanning speed: 0.2°/sec
Operation of the apparatus including data processing was performed by the method and procedure indicated for the apparatus.

<Simultaneous Thermogravimetry/Differential Thermal Analysis (TG/DTA)>

TG-DTA was conducted under the following test conditions.

Apparatus: Thermo Plus TG8120 (Rigaku. Corp.)
Sample: about 5 mg
Heating rate: 5° C./min
Operation of the apparatus including data processing was performed by the method and procedure indicated for the apparatus.

<Proton Nuclear Magnetic Resonance ($^1$H-NMR) Spectroscopy>

An examination by $^1$H-NMR spectroscopy was made with spectrometer Type AL400 (400 MHz; JEOL) or Mercury 400 (400 MHz; Agilent Technologies) or with spectrometer Type Inova 400 (400 MHz; Agilent Technologies) equipped with 400 MNMR Probe (Protasis), using tetramethylsilane as an internal reference in the case where tetramethylsilane was included in the heavy solvent or using the NMR solvent as an internal reference in the other cases. In each $^1$H-NMR chart obtained, all the δ values were shown in terms of ppm.

The abbreviations have the following meanings.
s: singlet
d: doublet
t: triplet
q: quartet
dd: double doublet
dt: double triplet
td: triple doublet
tt: triple triplet
ddd: double double doublet
ddt: double double triplet
dtd: double triple doublet
tdd: triple double doublet
m: multiplet
br: broad
brs: broad singlet <Liquid Chromatography (HPLC)>

An examination by liquid chromatography was made under the following test conditions.

Apparatus: Hitachi L-2455
Mobile phase A: 10 mM aqueous $Na_2HPO_4$ solution (pH, 6.5)
Mobile phase B: acetonitrile
Gradient: shown in Table 1
Column: GL Science Inertsil ODS-3; 4.6×150 mm; S=5 μm
Measuring wavelength: 220 nm
Operation of the apparatus including data processing was performed by the method and procedure indicated for the apparatus.

TABLE 1

| Time (min) | Mobile phase A (%) | Mobile phase B (%) |
|---|---|---|
| 0 | 55 | 45 |
| 10 | 40 | 60 |
| 12 | 10 | 90 |
| 15 | 10 | 90 |
| 17 | 55 | 45 |
| 25 | 55 | 45 |

Example 1; Mesylic Acid Salt of Compound 1

Acetone (80 mL), water (40 mL), and mesylic acid (3.71 g) were added to compound 1 (10.0 g) obtained by the method described in Patent Document 1, and the mixture was refluxed with heating for 1.5 hours. Thereafter, 30 mL of acetone was added thereto, and the resultant mixture was stirred at room temperature for 15 hours and subsequently at 0° C. for 3 hours. The insoluble matter which had precipitated during the stirring was taken out by filtration, thereby obtaining crystal of a mesylic acid salt of compound 1 (8.25 g; yield, 69%).

Figure 1:
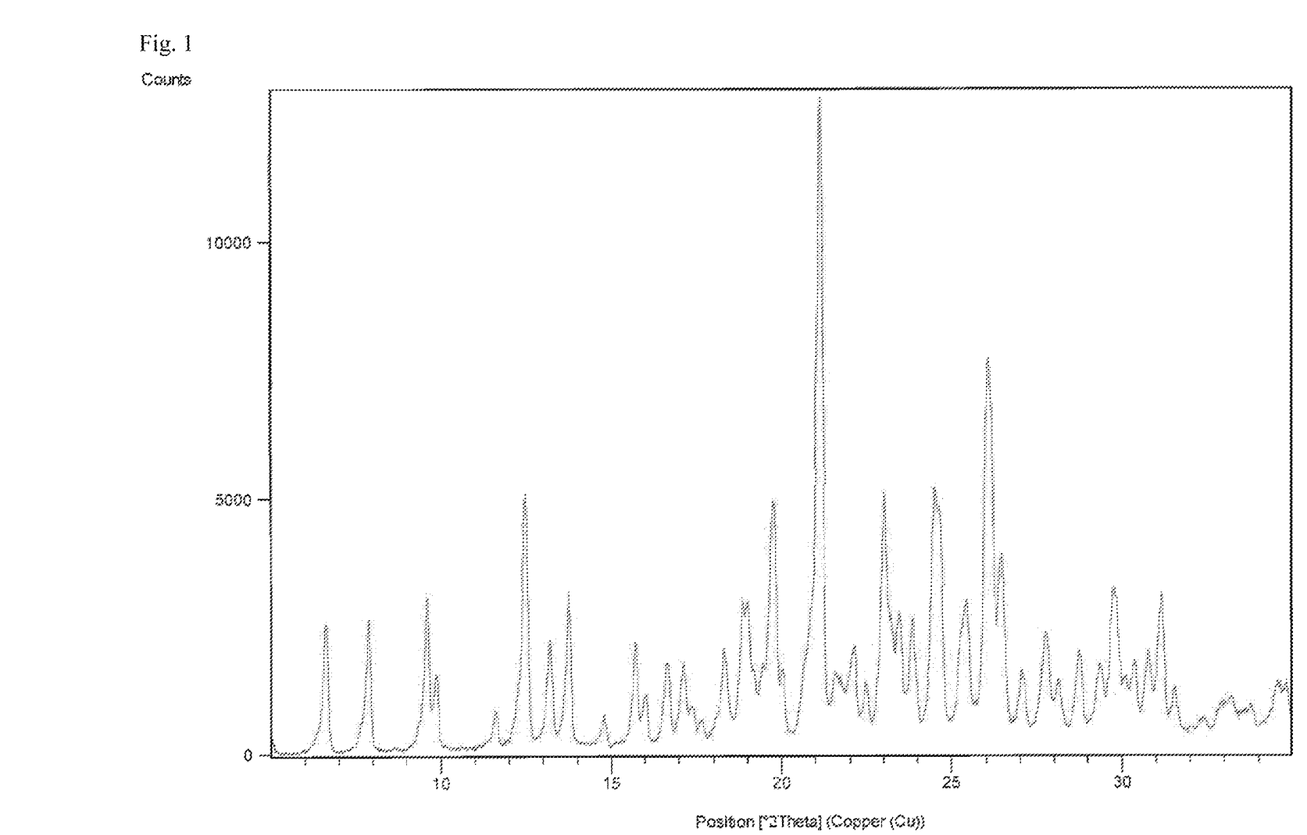
FIG. 1 shows an X-ray powder diffraction spectrum of a mesylic acid salt of compound 1 (ordinate indicates intensity (cps) and abscissa indicates diffraction angle (2θ)).
Figure 6:
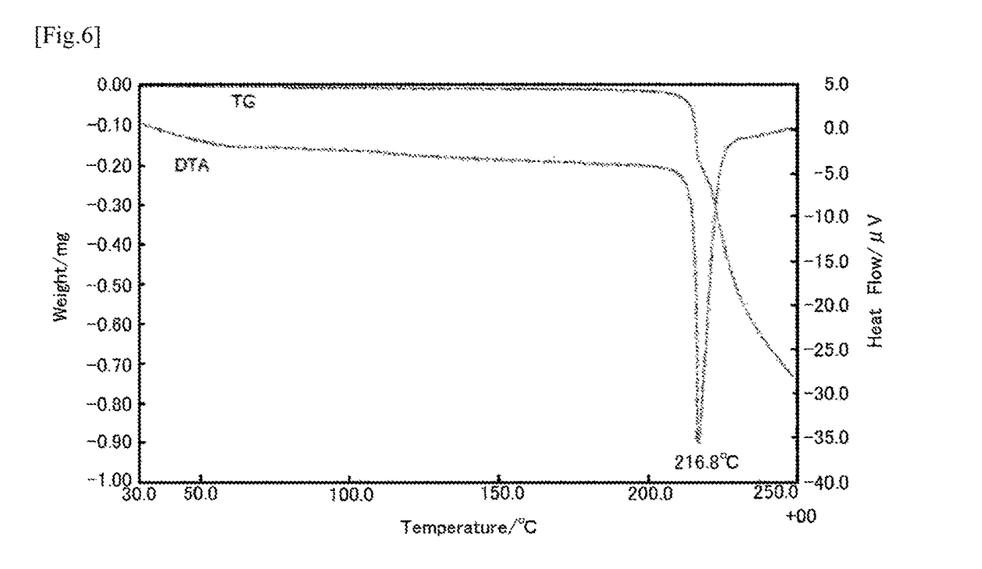
FIG. 6 shows the results of an examination of a mesylic acid salt of compound 1 by simultaneous thermogravimetry/differential thermal analysis (TG-DTA) (left-hand ordinate indicates weight (mg) for the TG curve, right-hand ordinate indicates heat flux (μV) for the DTA curve, and abscissa indicates temperature (° C.)).

An X-ray powder diffraction spectrum of the thus-obtained crystal of a mesylic acid salt of compound 1 is shown in FIG. 1. Specifically, peaks were observed at diffraction angles (2θ) of 6.7°, 7.9°, 9.6°, 11.6°, 12.5°, 13.2°, 13.8°, 14.8°, 15.7°, 19.8°, 21.2°, 23.0°, 24.5°, and 26.1°. A DTA curve thereof obtained by TG-DTA is shown in FIG. 6. The DTA curve had an endothermic peak at 217° C. (peak top value).

The compound obtained gave the following $^1$H-NMR spectrum.

¹H-NMR (400 MHz, DMSO-d₆): δ ppm 12.56 (1H, s), 11.87 (1H, s), 8.98 (1H, d, J=6.34 Hz), 8.69 (1H, s), 8.49 (1H, d, J=4.39 Hz), 8.13 (1H, d, J=11.47 Hz), 7.66-7.59 (3H, m), 7.39-7.28 (5H, m), 6.93 (1H, d, J=6.10 Hz), 4.07 (3H, s), 3.84 (3H, s), 2.83 (3H, d, J=3.90 Hz), 2.33 (3H, s)

In this Example, the crystal was not tenaciously adherent to the reaction vessel and no filter paper clogging therewith was observed in the filtration. Furthermore, in cases when compound 1 was used in an amount of 100 g, the synthesis was able to be performed similarly. The mesylic acid salt of compound 1 hence can be mass-produced.

In cases when methyl ethyl ketone or methyl isobutyl ketone was used in place of the acetone/water mixed solvent in this Example, the same mesylic acid salt of compound 1 was obtained.

Comparative Example 1; p-Tosic Acid Salt of Compound 1

Chloroform (100 mL), methanol (100 mL), and p-toluenesulfonic acid monohydrate (354 mg) were added to compound 1 (964 mg) obtained by the method described in Patent Document 1, and the mixture was stirred at room temperature. This mixture was then concentrated under vacuum to distill off the solvent. Thereafter, ethyl acetate was added to the residue, and the insoluble matter was taken out by filtration, thereby obtaining crystal of a p-toluenesulfonic acid (p-tosic acid) salt of compound 1 (1.24 g; yield, 97%).

Figure 2:
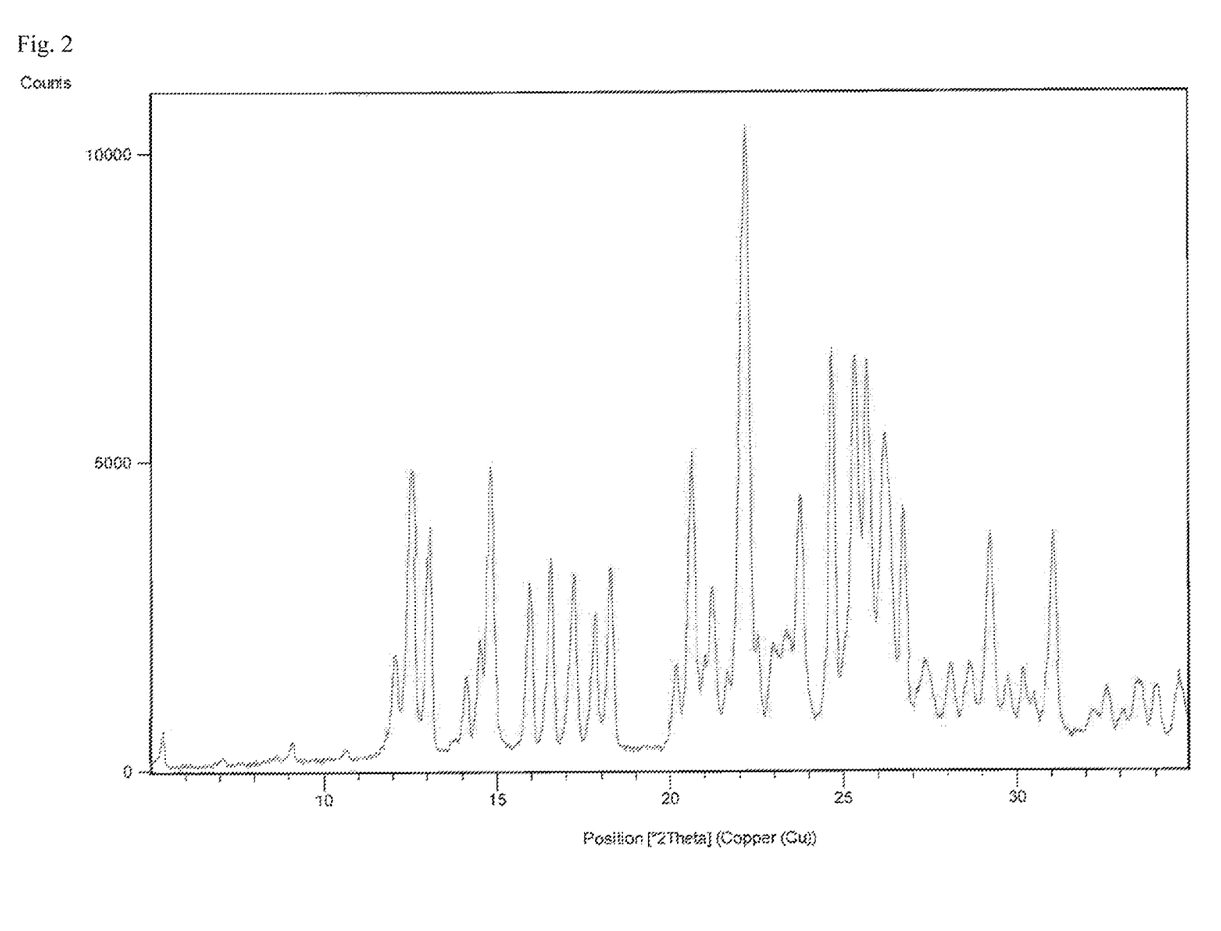
FIG. 2 shows an X-ray powder diffraction spectrum of a p-tosic acid salt of compound 1 (ordinate indicates intensity (cps) and abscissa indicates diffraction angle (2θ)).
Figure 7:
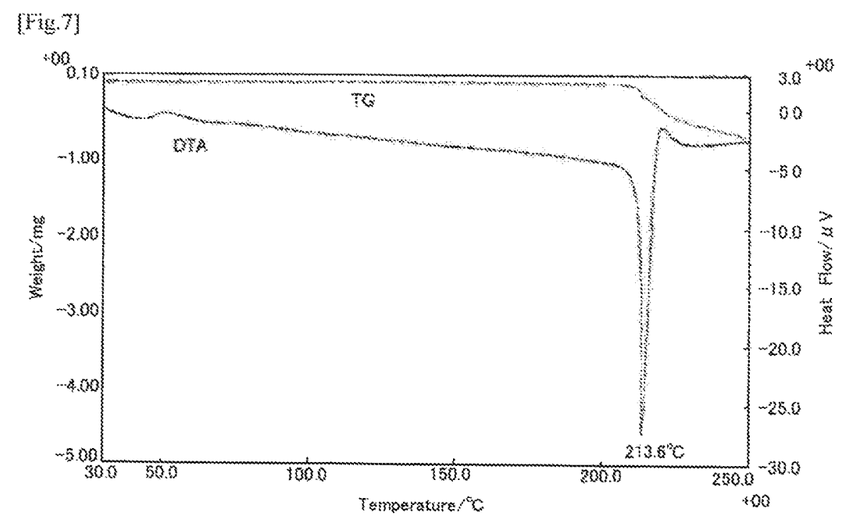
FIG. 7 shows the results of an examination of a p-tosic acid salt of compound 1 by simultaneous thermogravimetry/differential thermal analysis (TG-DTA) (left-hand ordinate indicates weight (mg) for the TG curve, right-hand ordinate indicates heat flux (N) for the DTA curve, and abscissa indicates temperature (° C.)).

An X-ray powder diffraction spectrum of the thus-obtained crystal of a p-tosic acid salt of compound 1 is shown in FIG. 2. Specifically, the crystals showed characteristic peaks at diffraction angles (2θ) of 12.6°, 14.9°, 20.7°, 22.3°, 24.7°, 25.4°, 25.7°, 26.2°, 29.2°, and 31.1°. A DTA curve thereof obtained by TG-DTA is shown in FIG. 7. The DTA curve had an endothermic peak at 214° C. (peak top value).

The compound obtained gave the following ¹H-NMR spectrum. From the integral of a peak attributable to p-tosic acid, the molar ratio between compound 1 and p-tosic acid was deemed to be 1:1.

¹H-NMR (400 MHz, DMSO-d6): δ ppm 12.56 (1H, s), 11.87 (1H, s), 8.98 (1H, d, J=6.34 Hz), 8.69 (1H, s), 8.49 (1H, d, J=4.39 Hz), 8.15-8.10 (1H, m), 7.66-7.59 (3H, m), 7.48 (2H, d, J=8.05 Hz), 7.39-7.29 (4H, m), 7.11 (2H, d, J=7.81 Hz), 6.92 (1H, d, J=6.10 Hz), 4.07 (3H, s), 3.84 (3H, s), 2.84 (3H, d, J=4.88 Hz), 2.28 (3H, s)

Comparative Example 2; Hydrochloric Acid Salt of Compound 1

Compound 1 (1.02 g) and 6-N aqueous hydrochloric acid solution (361 μL) were used to obtain crystal of a hydrochloric acid salt of compound 1 in the same manner as in Comparative Example 1.

Figure 3:
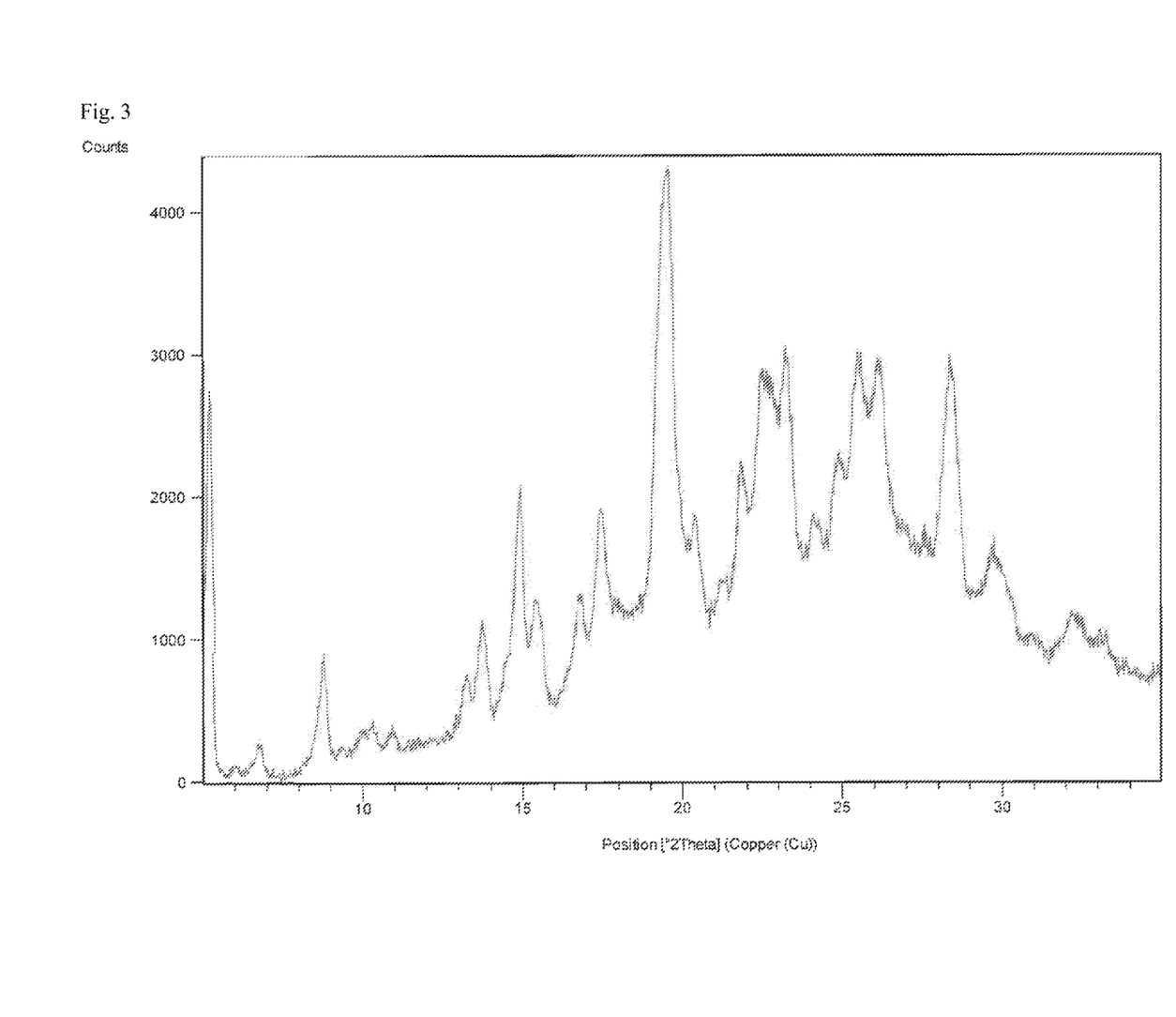
FIG. 3 shows an X-ray powder diffraction spectrum of a hydrochloric acid salt of compound 1 (ordinate indicates intensity (cps) and abscissa indicates diffraction angle (2θ)).
Figure 8:
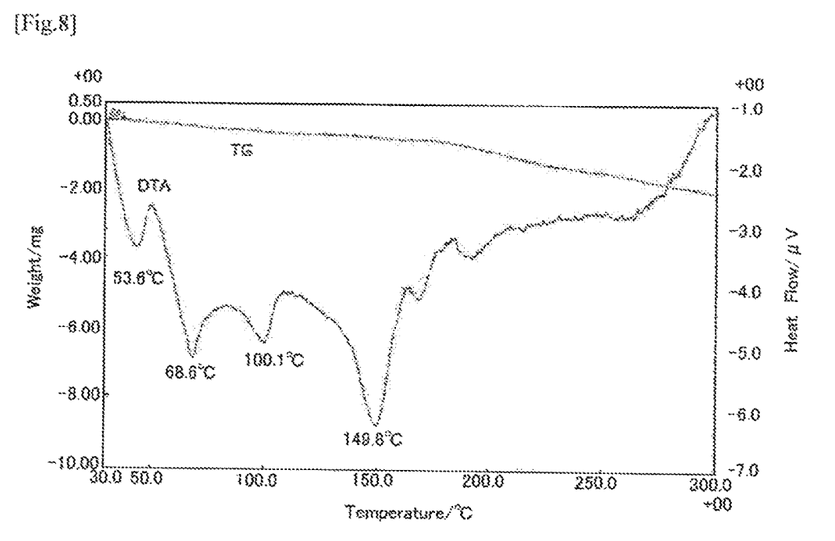
FIG. 8 shows the results of an examination of a hydrochloric acid salt of compound 1 by simultaneous thermogravimetry/differential thermal analysis (TG-DTA) (left-hand ordinate indicates weight (mg) for the TG curve, right-hand ordinate indicates heat flux (μV) for the DTA curve, and abscissa indicates temperature (° C.)).

An X-ray powder diffraction spectrum of the thus-obtained crystals of a hydrochloric acid salt of compound 1 is shown in FIG. 3. Specifically, the crystal showed characteristic peaks at diffraction angles (2θ) of 5.2°, 14.9°, 17.5°, 19.6°, 22.5°, 23.3°, 25.5°, 26.2°, and 28.5°. A DTA curve thereof obtained by TG-DTA is shown in FIG. 8. The DTA curve had a plurality of overlapped minor peaks, showing that the salt was lowly crystalline.

The compound obtained gave the following ¹H-NMR spectrum.

¹H-NMR (400 MHz, DMSO-d6): δ ppm 12.54 (1H, s), 11.85 (1H, s), 8.93 (1H, d, J=6.10 Hz), 8.66 (1H, s), 8.50-8.45 (1H, m), 8.10 (1H, d, J=13.17 Hz), 7.67 (1H, s), 7.64-7.57 (2H, m), 7.37-7.27 (4H, m), 6.87 (1H, d, J=6.34 Hz), 4.06 (3H, s), 3.83 (3H, s), 2.83 (3H, d, J=4.64 Hz)

Reference Example 1; Crystal I of Compound 1

N,N-diethylacetamide (18 mL) was added to compound 1 (3.00 g) obtained by the method described in Patent Document 1, and the mixture was stirred at 50° C. for 5 minutes. Thereafter, isopropanol (54 mL) was added thereto, and the resultant mixture was stirred at room temperature for 3 hours. The precipitate was taken out by filtration, thereby obtaining crystal I of compound 1 (2.41 g; yield, 80%).

Figure 4:
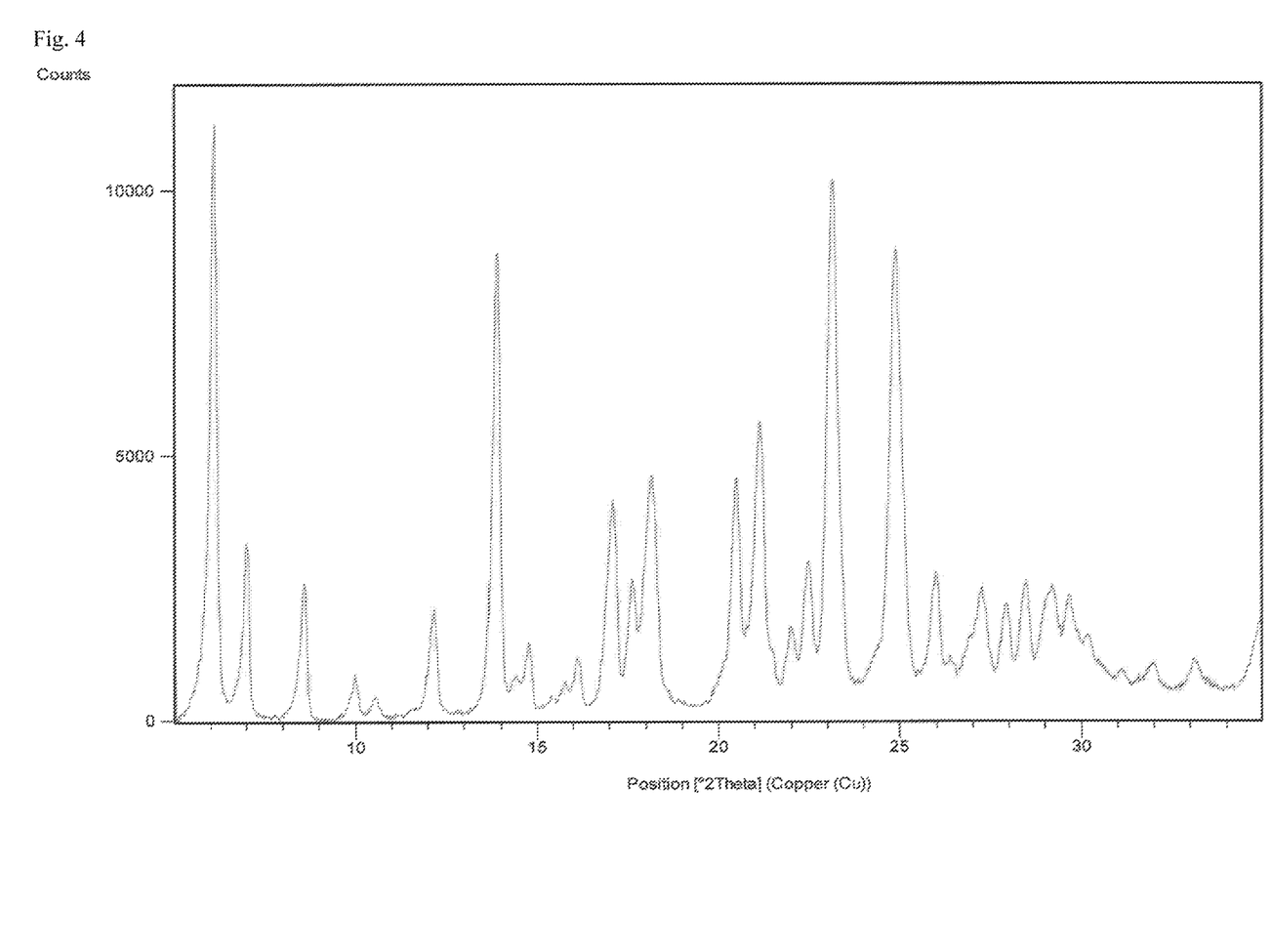
FIG. 4 shows an X-ray powder diffraction spectrum of crystal I of compound 1 (ordinate indicates intensity (cps) and abscissa indicates diffraction angle (2θ)).
Figure 9:
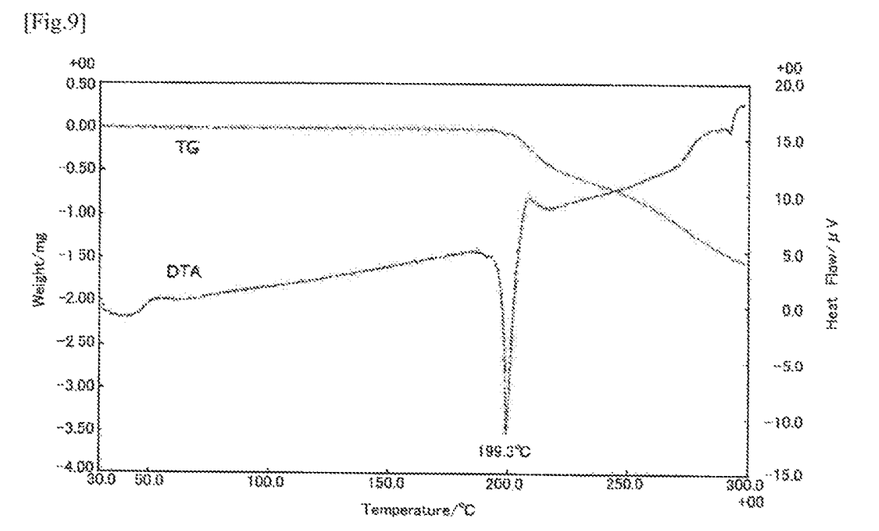
FIG. 9 shows the results of an examination of crystal I of compound 1 by simultaneous thermogravimetry/differential thermal analysis (TG-DTA) (left-hand ordinate indicates weight (mg) for the TG curve, right-hand ordinate indicates heat flux (μV) for the DTA curve, and abscissa indicates temperature (° C.)).

An X-ray powder diffraction spectrum of the thus-obtained crystal I of compound 1 is shown in FIG. 4. Specifically, the crystal I showed characteristic peaks at diffraction angles (2θ) of 6.1°, 13.9°, 23.2°, and 24.9°. A DTA curve thereof obtained by TG-DTA is shown in FIG. 9. The DTA curve had an endothermic peak at 199° C. (peak top value).

Comparative Example 3; Crystal II of Compound 1

Ethanol (26.4 mL) was added to the crystal I of compound 1 obtained in Reference Example 1 (2.20 g), and the mixture was refluxed with heating for 2 hours. Thereafter, the mixture was allowed to cool to room temperature, and the precipitate was taken out by filtration, thereby obtaining crystal II of compound 1 (1.91 g; yield, 87%).

Figure 5:
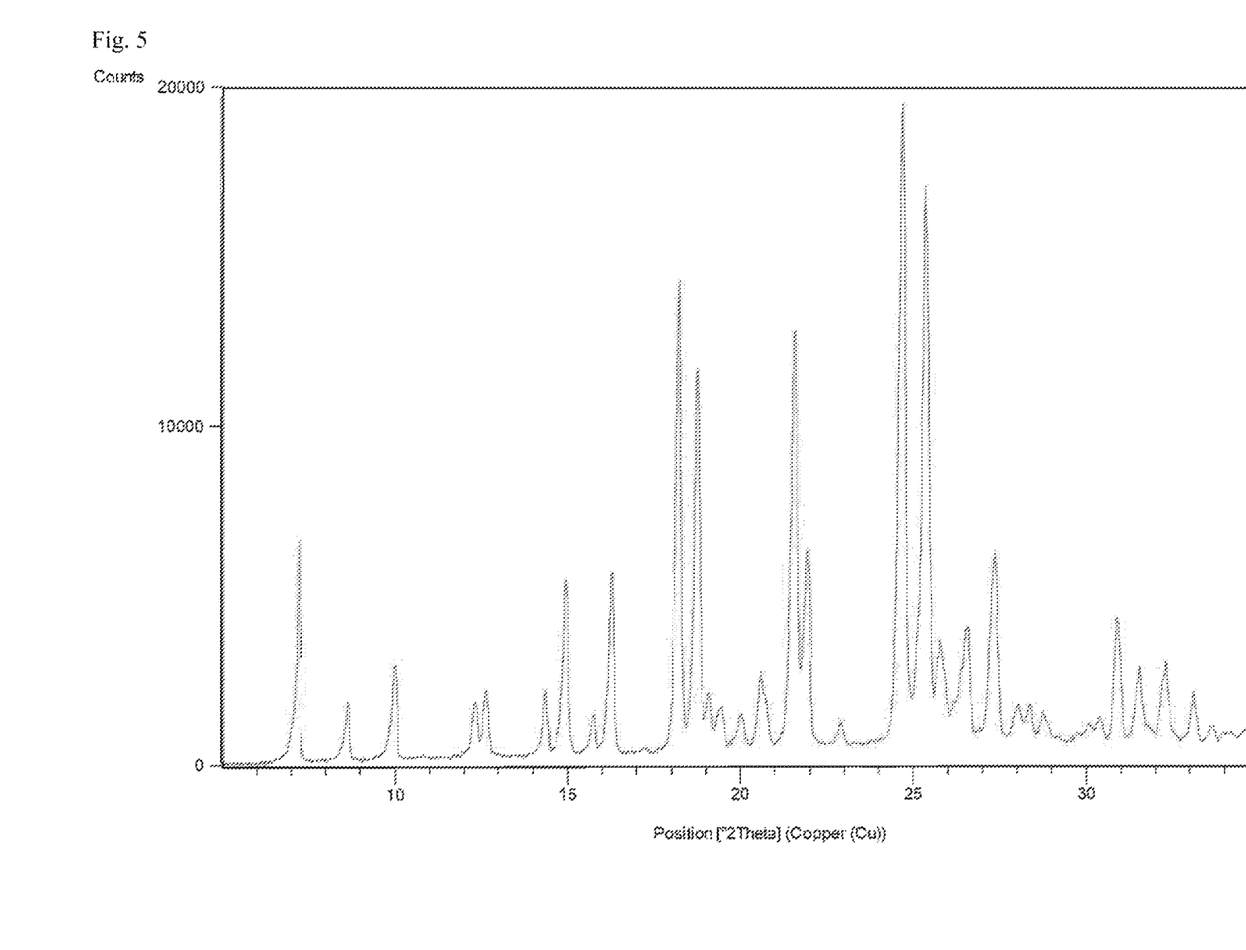
FIG. 5 shows an X-ray powder diffraction spectrum of crystal II of compound 1 (ordinate indicates intensity (cps) and abscissa indicates diffraction angle (2θ)).
Figure 10:
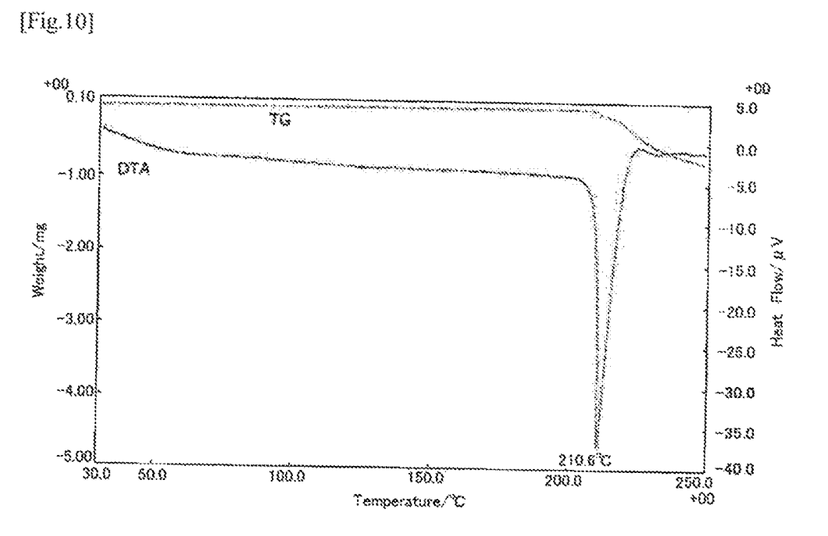
FIG. 10 shows the results of an examination of crystal II of compound 1 by simultaneous thermogravimetry/differential thermal analysis (TG-DTA) (left-hand ordinate indicates weight (mg) for the TG curve, right-hand ordinate indicates heat flux (N) for the DTA curve, and abscissa indicates temperature (° C.)).

An X-ray powder diffraction spectrum of the thus-obtained crystal II of compound 1 is shown in FIG. 5. Specifically, the crystal II showed characteristic peaks at diffraction angles (2θ) of 7.3°, 18.3°, 18.8°, 21.6°, 24.7°, and 25.3°. A DTA curve thereof obtained by TG-DTA is shown in FIG. 10. The DTA curve had an endothermic peak at 211° C. (peak top value).

Test Example 1

An examination by liquid chromatography was conducted for the purpose of selecting, by screening, acids expected to attain an improvement in solubility from among acids capable of forming salts with compound 1. Compound 1 (5 mg) and an acid (5 mg) were added to water (5 mL), and the mixture was stirred at room temperature for 1 hour. This solution of compound 1 was examined by liquid chromatography. The acid concentration in the solution of compound 1 was determined by comparing the areas of peaks of the chromatogram obtained. The acids used were mesylic acid, p-tosic acid, hydrochloric acid, oxalic acid, malonic acid, tartaric acid, citric acid, mandelic acid, fumaric acid, aspartic acid, sulfuric acid, malic acid, hippuric acid, glutaric acid, adipic acid, succinic acid, ascorbic acid, maleic acid, and isoascorbic acid. In the case of hydrochloric acid, however, compound 1 (5 mg) was added to 0.1-N aqueous hydrochloric acid solution (5 mL).

As a result, mesylic acid, p-tosic acid, and hydrochloric acid were found to be the only acids in which the peak areas were far larger than those of the other acids. These acids were hence deemed to be acids that gave salts with compound 1 which were expected to have improved solubility.

Test Example 2; Solubility Measurement

Salts of compound 1 which were formed using mesylic acid, p-tosic acid, and hydrochloric acid were examined for solubility. Specifically, the crystal of a mesylic acid salt of compound 1 produced in Example 1, the crystal of a p-tosic acid salt of compound 1 produced in Comparative Example 1, the crystal of a hydrochloric acid salt of compound 1 produced in Comparative Example 2, and the crystal II of compound 1 were used as samples and examined, in accordance with the solubility measuring method as provided for in The Japanese Pharmacopoeia, for solubility in the dissolution-test second liquid according to The Japanese Pharmacopoeia, purified water, 20-mM aqueous taurocholic acid solution, and FeSSIF (*Pharm Res.*, 1998, May; 15(5); 698-705). The results are shown in Table 2. It was found from the results that the mesylic acid salt of compound 1 is superior in solubility to the other salts and the free form. In particular, since the mesylic acid salt showed high solubility in FeSSIF, which is one of the intestinal solutions, it was suggested that this salt might have enhanced intestinal absorbability. This salt was deemed to be suitable for medicine development.

TABLE 2

| | Solubility (μg/mL, 37° C.) | | | |
|---|---|---|---|---|
| | Dissolution-test second liquid | Purified water | Taurocholic acid | FeSSIF |
| Example 1 | 1.0 | 35 | 120 | 11 |
| Comparative Example 1 | nd | 3.5 | 64 | 8.0 |
| Comparative Example 2 | nd | 23 | 65 | 2.1 |
| Comparative Example 3 | nd | nd | 2.8 | 6.1 | nd: ≤0.5 μg/mL

Test Example 3; Solid Stability Test

The crystals of a mesylic acid salt of compound 1 produced in Example 1 was allowed to stand for 1 month under the conditions of 40° C. (open system), 40° C. (humidity, 75%), or 60° C. (open system). Thereafter, the crystals were examined for purity by liquid chromatography. As a result, the change in purity through the test was 0.1% or less under all those conditions. Furthermore, no marked change was observed in examinations by XRD and TG-DTA.

From these results, the crystal of a mesylic acid salt of compound 1 was deemed to be crystal which as a solid had excellent stability.

While the invention has been described in detail and with reference to specific embodiments thereof, it will be apparent to one skilled in the art that various changes and modifications can be made therein without departing from the spirit and scope thereof. This application is based on a Japanese patent application filed on Apr. 30, 2015 (Application No. 2015-092815), the contents thereof being incorporated herein by reference.

INDUSTRIAL APPLICABILITY

Compound 1 in the invention is a compound which has c-Met/VEGFR inhibitory activity and shows excellent antitumor activity, and the mesylic acid salt thereof is excellent in terms of solubility and peroral absorbability. Furthermore, crystal of the salt are excellent in terms of solubility, stability, and peroral absorbability and can be mass-produced. Because of this, the mesylic acid salt of compound 1 or crystal of the salt can be expected to be utilized as medicines especially for oral administration, in particular, antitumor agents for oral administration.

The invention claimed is:

1. A crystalline mesylic acid salt of 4-(2-fluoro-4-(3-(2-phenylacetyl)thioureido)phenoxy)-7-methoxy-N-methylquinoline-6-carboxamide having an X-ray powder diffraction spectrum with characteristic peaks at at least three diffraction angles (2θ±0.2°) selected from the group consisting of 6.7°, 7.9°, 9.6°, 12.5°, 13.8°, 19.8°, 21.2°, and 26.1°.

2. The crystalline mesylic acid salt according to claim 1, having an X-ray powder diffraction spectrum with characteristic peaks at at least five diffraction angles (2θ±0.2°) selected from the group consisting of 6.7°, 7.9°, 9.6°, 12.5°, 13.8°, 19.8°, 21.2°, and 26.1°.

3. The crystalline mesylic acid salt according to claim 1, having an X-ray powder diffraction spectrum with characteristic peaks at diffraction angles (2θ±0.2°) of 6.7°, 7.9°, 9.6°, 12.5°, 13.8°, 19.8°, 21.2°, and 26.1°.

4. The crystalline mesylic acid salt according to claim 1, which shows an endothermic peak at 217±5° C. in differential thermal analysis.

5. A medicinal composition which comprises an effective amount of the crystalline mesylic acid salt according to claim 1, and a pharmaceutically acceptable carrier.

6. A medicinal composition which comprises an effective amount of the crystalline mesylic acid salt according to claim 1, and a pharmaceutically acceptable carrier, wherein the medicinal composition is suitable for oral administration.

7. A process for producing a crystalline mesylic acid salt of 4-(2-fluoro-4-(3-(2-phenylacetyl)thioureido)phenoxy)-7-methoxy-N-methylquinoline-6-carboxamide, the process comprising:
    adding 4-(2-fluoro-4-(3-(2-phenylacetyl)thioureido)phenoxy)-7-methoxy-N-methylquinoline-6-carboxamide and mesylic acid to a solvent, to obtain a mixture; and
    stirring the mixture to precipitate a crystalline mesylic acid salt of 4-(2-fluoro-4-(3-(2-phenylacetyl)thioureido)phenoxy)-7-methoxy-N-methylquinoline-6-carboxamide,
    wherein the crystalline mesylic acid salt of 4-(2-fluoro-4-(3-(2-phenylacetyl)thioureido)phenoxy)-7-methoxy-N-methylquinoline-6-carboxamide has an X-ray powder diffraction spectrum with characteristic peaks at at least three diffraction angles (2θ±0.2°) selected from the group consisting of 6.7°, 7.9°, 9.6°, 12.5°, 13.8°, 19.8°, 21.2°, and 26.1°.

8. The process according to claim 7, wherein the crystalline mesylic acid salt of 4-(2-fluoro-4-(3-(2-phenylacetyl)thioureido)phenoxy)-7-methoxy-N-methylquinoline-6-carboxamide has an X-ray powder diffraction spectrum with characteristic peaks at at least five diffraction angles (2θ+0.2°) selected from the group consisting of 6.7°, 7.9°, 9.6°, 12.5°, 13.8°, 19.8°, 21.2°, and 26.1°.

9. The process according to claim 7, wherein the crystalline mesylic acid salt of 4-(2-fluoro-4-(3-(2-phenylacetyl)thioureido)phenoxy)-7-methoxy-N-methylquinoline-6-carboxamide has an X-ray powder diffraction spectrum with characteristic peaks at diffraction angles (2θ+0.2°) of 6.7°, 7.9°, 9.6°, 12.5°, 13.8°, 19.8°, 21.2°, and 26.1°.

10. The process according to claim 7, wherein the crystalline mesylic acid salt of 4-(2-fluoro-4-(3-(2-phenylacetyl)thioureido)phenoxy)-7-methoxy-N-methylquinoline-6-carboxamide shows an endothermic peak at 217±5° C. in differential thermal analysis.

11. The process according to claim 7, wherein the solvent is at least one solvent selected from the group consisting of water, an alcohol, an aliphatic carboxylic acid ester, a ketone, an ether, a hydrocarbon, and an aprotic polar solvent.

12. The process according to claim 7, wherein the solvent is at least one solvent selected from the group consisting of water, an alcohol, an aliphatic carboxylic acid ester, and a ketone.

13. The process according to claim 7, wherein the solvent is ethanol, isopropanol, ethyl acetate, acetone, methyl ethyl ketone, methyl isobutyl ketone, or an acetone/water mixed solvent.

14. A crystalline mesylic acid salt of 4-(2-fluoro-4-(3-(2-phenylacetyl)thioureido)phenoxy)-7-methoxy-N-methylquinoline-6-carboxamide, wherein the crystalline mesylic acid salt is produced by a process comprising:
adding 4-(2-fluoro-4-(3-(2-phenylacetyl)thioureido)phenoxy)-7-methoxy-N-methylquinoline-6-carboxamide and mesylic acid to a solvent, to obtain a mixture; and
stirring the mixture to precipitate a crystalline mesylic acid salt of 4-(2-fluoro-4-(3-(2-phenylacetyl)thioureido)phenoxy)-7-methoxy-N-methylquinoline-6-carboxamide,
wherein the crystalline mesylic acid salt has an X-ray powder diffraction spectrum with characteristic peaks at at least three diffraction angles (2θ±0.2°) selected from the group consisting of 6.7°, 7.9°, 9.6°, 12.5°, 13.8°, 19.8°, 21.2°, and 26.1°.

15. The crystalline mesylic acid salt according to claim 14, having an X-ray powder diffraction spectrum with characteristic peaks at at least five diffraction angles (2θ±0.2°) selected from the group consisting of 6.7°, 7.9°, 9.6°, 12.5°, 13.8°, 19.8°, 21.2°, and 26.1°.

16. The crystalline mesylic acid salt according to claim 14, having an X-ray powder diffraction spectrum with characteristic peaks at diffraction angles (2θ±0.2°) of 6.7°, 7.9°, 9.6°, 12.5°, 13.8°, 19.8°, 21.2°, and 26.1°.

17. The crystalline mesylic acid salt according to claim 14, which shows an endothermic peak at 217±5° C. in differential thermal analysis.

18. The crystalline mesylic acid salt according to claim 14, wherein the solvent is at least one solvent selected from the group consisting of water, an alcohol, an aliphatic carboxylic acid ester, a ketone, an ether, a hydrocarbon, and an aprotic polar solvent.

19. The crystalline mesylic acid salt according to claim 14, wherein the solvent is at least one solvent selected from the group consisting of water, an alcohol, an aliphatic carboxylic acid ester, and a ketone.

20. The crystalline mesylic acid salt according to claim 14, wherein the solvent is ethanol, isopropanol, ethyl acetate, acetone, methyl ethyl ketone, methyl isobutyl ketone, or an acetone/water mixed solvent.

* * * * *